US009529007B2

(12) United States Patent
Mizumoto et al.

(10) Patent No.: US 9,529,007 B2
(45) Date of Patent: Dec. 27, 2016

(54) ANALYZING APPARATUS, ANALYZING METHOD AND A NON-TRANSITORY STORAGE MEDIUM

(75) Inventors: Toru Mizumoto, Kobe (JP); Hiroo Tatsutani, Kobe (JP)

(73) Assignee: Sysmex Corporation (JP)

(*) Notice: Subject to any disclaimer, the term of this patent is extended or adjusted under 35 U.S.C. 154(b) by 379 days.

(21) Appl. No.: 12/870,455

(22) Filed: Aug. 27, 2010

(65) Prior Publication Data

US 2011/0054807 A1 Mar. 3, 2011

(30) Foreign Application Priority Data

Aug. 28, 2009 (JP) ................................ 2009-199054

(51) Int. Cl.
| | | |
|---|---|---|
| G01N 33/48 | (2006.01) | |
| G01N 33/50 | (2006.01) | |
| G01R 23/00 | (2006.01) | |
| G01N 35/00 | (2006.01) | |
| G01N 15/14 | (2006.01) | |
| G01N 35/04 | (2006.01) | |

(52) U.S. Cl.
CPC ......... G01N 35/00623 (2013.01); G01R 23/00 (2013.01); *G01N 15/1459* (2013.01); *G01N 2035/00653* (2013.01); *G01N 2035/0415* (2013.01)

(58) Field of Classification Search
CPC .......... G01R 23/00; G01R 23/16; G01N 35/00
USPC ............................................. 702/76, 117, 75
See application file for complete search history.

(56) References Cited

U.S. PATENT DOCUMENTS

| | | | | |
|---|---|---|---|---|
| 4,653,078 A | * | 3/1987 | Aritomi | ............ G01N 15/1459 |
| | | | | 324/71.4 |
| 2001/0028473 A1 | * | 10/2001 | Yamasaki | ........... G06F 11/0709 |
| | | | | 358/1.15 |

(Continued)

FOREIGN PATENT DOCUMENTS

| | | |
|---|---|---|
| CN | 1613014 A | 5/2005 |
| CN | 101135692 A | 3/2008 |

(Continued)

OTHER PUBLICATIONS

Xiaohong, Shang et al., "The study to the co-intervention and cross-contamination of Hitachi 7600-020 Automatic bio-Chemical Analysis Instrument," China Medical Equipment, Nov. 2007, vol. 4, No. 11, pp. 17-24.

*Primary Examiner* — Michael Nghiem
(74) *Attorney, Agent, or Firm* — Brinks Gilson & Lione

(57) ABSTRACT

An analyzing apparatus comprising a processor of a controller and a memory that stores programs executable by the processor to: receive a test result on a test item from a measurement unit; analyze the test result to determine whether the test result indicates an abnormality on the test item; if the test result is determined to indicate an abnormality on the test item, update a history database in which a history of abnormality determinations made on the test item is recorded; review the history database to determine whether a frequency of abnormality determinations made on the test item exceeds a predetermined frequency for the test item; and if the frequency of abnormality is determined to exceed the predetermined frequency for the test item, alert a user on a possible problem is disclosed. An analyzing method and a non-transitory storage medium are also disclosed.

10 Claims, 15 Drawing Sheets

(56) References Cited

U.S. PATENT DOCUMENTS

| | | | |
|---|---|---|---|
| 2004/0037428 A1* | 2/2004 | Keller | 381/60 |
| 2004/0224351 A1 | 11/2004 | Shinohara | |
| 2005/0157327 A1* | 7/2005 | Shoji et al. | 358/1.14 |
| 2005/0175503 A1* | 8/2005 | Shiba et al. | 422/64 |
| 2006/0012787 A1* | 1/2006 | Nakayama | G01N 15/1459 356/336 |
| 2007/0048868 A1* | 3/2007 | Shibata et al. | 436/43 |
| 2007/0183926 A1* | 8/2007 | Tanoshima | 422/65 |
| 2007/0257806 A1* | 11/2007 | Madden et al. | 340/603 |
| 2008/0056944 A1 | 3/2008 | Nakamura et al. | |
| 2009/0093045 A1* | 4/2009 | Takenaka | G01N 15/147 435/287.1 |
| 2009/0132858 A1* | 5/2009 | Koeda et al. | 714/37 |
| 2009/0215183 A1* | 8/2009 | Takehara et al. | 436/47 |
| 2009/0292492 A1* | 11/2009 | Nishida et al. | 702/85 |
| 2010/0010787 A1* | 1/2010 | Suematsu et al. | 703/2 |
| 2010/0127885 A1* | 5/2010 | Okuno et al. | 340/825.22 |
| 2010/0290950 A1* | 11/2010 | Nakaya et al. | 422/67 |
| 2011/0244557 A1* | 10/2011 | Hamada | 435/286.1 |

FOREIGN PATENT DOCUMENTS

| | | |
|---|---|---|
| JP | 06-011511 A | 1/1994 |
| JP | 2003-083960 A | 3/2003 |
| JP | 2003-232797 A | 8/2003 |

\* cited by examiner

FIG. 10

| ENTRY | NUMBER OF OCCURRENCES |
|---|---|
| PLT Clumps? | 3 |
| XXX | 4 |
| YYY | 2 |
| ZZZ | 1 |
| ⋮ | ⋮ |

ANALYZING APPARATUS, ANALYZING METHOD AND A NON-TRANSITORY STORAGE MEDIUM

RELATED APPLICATIONS

This application claims priority under 35 U.S.C. §119 to Japanese Patent Application No. 2009-199054 filed on Aug. 28, 2009, the entire content of which is hereby incorporated by reference.

FIELD OF THE INVENTION

The present invention relates to an analyzing apparatus, an analyzing method and a non-transitory storage medium used to analyze a sample obtained from a test subject.

BACKGROUND OF THE INVENTION

Japanese laid-open patent publication 2003-083960 discloses a blood analyzing apparatus for analyzing a component of blood obtained from a test subject, having an electromagnetic valve, a pipette, and a flow channel. The blood analyzing apparatus monitors the electromagnetic valve and the pipette using a sensor. When any abnormal status is detected by the sensor, the blood analyzing apparatus generates an alarm to notify a user the abnormal status generated in the analyzing apparatus.

Some structural elements provided in a conventional blood analyzing apparatus do not produce any motion unlike the electromagnetic valve which is opened or closed or the pipette which is transferred in the analyzing apparatus. However, they occasionally go wrong. The blood analyzing apparatus, however, can only detect any problem generated therein by using the sensor, therefore, conventionally had difficulty in detecting any problematic section which neither opens/closes nor moves.

SUMMARY OF THE INVENTION

The scope of the present invention is defined solely by the appended claims, and is not affected to any degree by the statements within this summary.

A first aspect of the present invention is an analyzing apparatus comprising a processor of a controller and a memory that stores programs executable by the processor to: receive a test result on a test item from a measurement unit configured to test a sample on at least one test item; analyze the test result to determine whether the test result indicates an abnormality on the test item; if the test result is determined to indicate an abnormality on the test item, update a history database in which a history of abnormality determinations made on the test item is recorded; review the history database to determine whether a frequency of abnormality determinations made on the test item exceeds a predetermined frequency for the test item; and if the frequency of abnormality determinations made on the test item is determined to exceed the predetermined frequency for the test item, alert a user on a possible problem sustained by the measurement unit.

A second aspect of the present invention is a method for detecting a possible problem of an analyzing apparatus, comprising computer executable steps executed by a processor of a controller to implement: receiving a test result on a test item from a measurement unit configured to test a sample on at least one test item; analyzing the test result to determine whether the test result indicates an abnormality on the test item; if the test result is determined to indicate an abnormality on the test item, updating a history database in which a history of abnormality determinations made on the test item is recorded; reviewing the history database to determine whether a frequency of abnormality determinations made on the test item exceeds a predetermined frequency for the test item; and if the frequency of abnormality determinations made on the test item is determined to exceed the predetermined frequency for the test item, alerting a user on a possible problem sustained by the measurement unit.

A third aspect of the present invention is a non-transitory storage medium which comprises programs executable by a processor of a controller to: receive a test result on a test item from a measurement unit configured to test a sample on at least one test item; analyze the test result to determine whether the test result indicates an abnormality on the test item; if the test result is determined to indicate an abnormality on the test item, update a history database in which a history of abnormality determinations made on the test item is recorded; review the history database to determine whether a frequency of abnormality determinations made on the test item exceeds a predetermined frequency for the test item; and if the frequency of abnormality determinations made on the test item is determined to exceed the predetermined frequency for the test item, alert a user on a possible problem sustained by the measurement unit.

BRIEF DESCRIPTION OF THE DRAWINGS

FIG. 10 illustrates an abnormality occurrence history database according to the exemplary embodiment.

DETAILED DESCRIPTION OF THE EMBODIMENT

An automatic analyzing apparatus according to an exemplary embodiment of the present invention is a hemocyte analyzing apparatus for sorting and calculating different hemocyte components included in a blood sample collected from a test subject, such as red blood cells, white blood cells and platelets.

Figure 1:
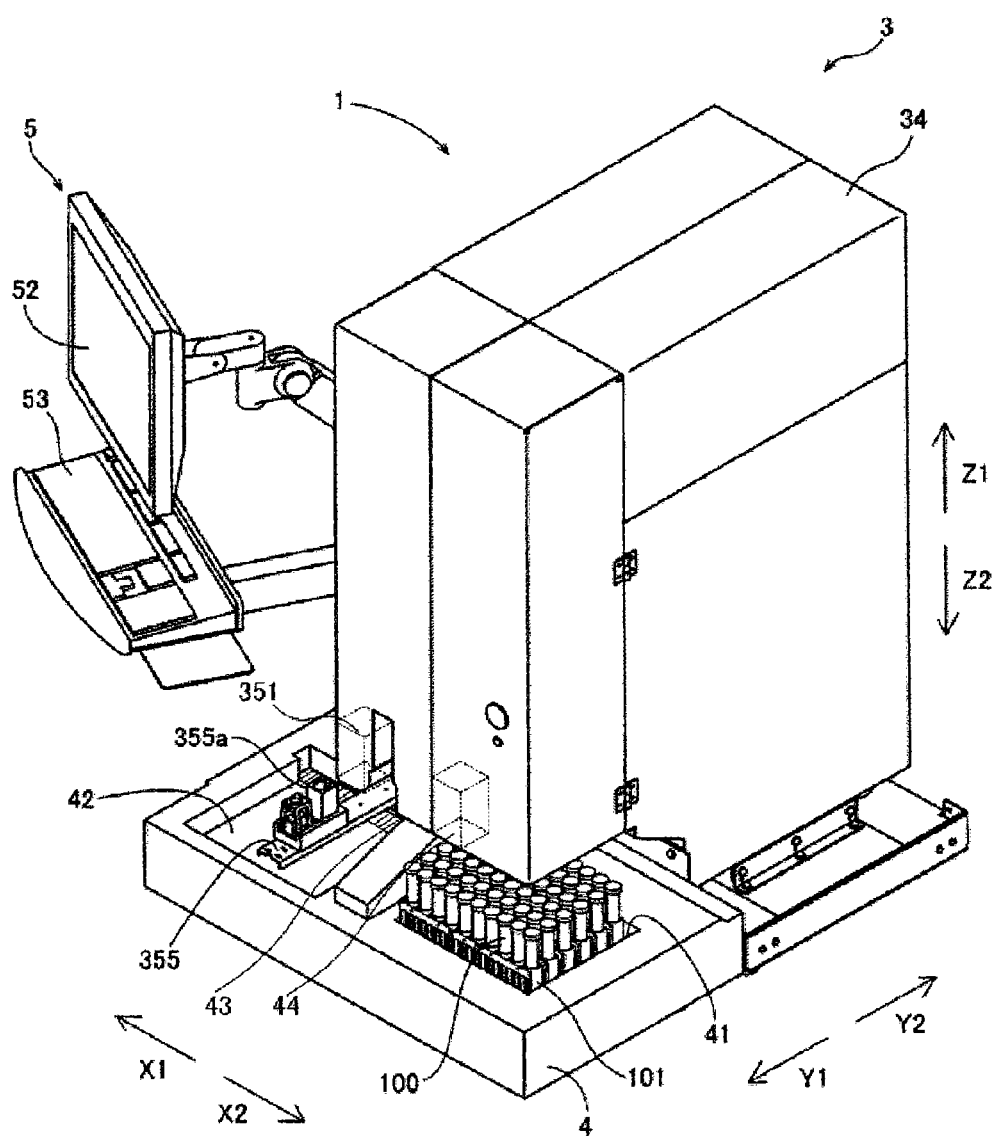
FIG. 1 is a perspective view illustrating an external appearance of an automatic analyzing apparatus according to an exemplary embodiment of the present invention.

FIG. 1 is a perspective view illustrating an external appearance of an automatic analyzing apparatus 1. As illustrated in FIG. 1, the hemocyte analyzing apparatus 1 includes a measurement unit 3, a conveying unit 4, and a controller 5. The conveying unit 4 is disposed on a front-surface side of the measurement unit 3 (on a side of the apparatus arrow—Y1 direction). The controller 5 is electrically connected to the measurement unit 3 and the conveying unit 4. The controller 5 includes a personal computer, and further includes a display device 52 and an input device 53. The display device 52 is provided to display an analysis result obtained by analyzing data of digital signals transmitted from the measurement unit 3.

The measurement unit 3 includes a hand portion 351 by which a sample container 100 can be held, and a sample container transfer portion 355 for horizontally moving the sample container 100 in the directions of arrows Y1 and Y2. The hand portion 351 is movable in vertical directions (directions of arrows Z1 and Z2) and horizontal directions (directions of arrows X1 and X2). The sample container transfer portion 355 includes a sample setter 355a. The sample container transfer portion 355 slides in the direction of arrow Y2 so that the sample setter 355a is placed at a sample suctioning position where the sample is suctioned by a sample suctioning section 31 described later. The hand portion 351, sample container transfer portion 355, and sample setter 355a are included in a sample container conveying section 35 described later (see FIG. 3).

The conveying unit 4 includes a pre-analysis rack retaining section 41 which can retain a plurality of racks 101 retaining therein the sample containers 100 in which pre-analysis samples are contained, a post-analysis rack retaining section 42 which can retain a plurality of racks 101 retaining therein the sample containers 100 in which post-analysis samples are contained, a conveying section 43 capable of transversely conveying the rack 101 in the directions of X1 and X2, and a barcode reader 44 which reads a barcode 100b of the sample container 100 and a barcode 101a bonded to each of the racks 101.

The rack conveying section 43 can uninterruptedly convey the racks 101 retained in the pre-analysis rack retaining section 41 in the direction of arrow X1. The rack conveying section 43 conveys the rack 101 retained in the pre-analysis rack retaining section 41 to a sample feeding position. The sample feeding position is a position at which the sample container 100 retained in the rack 101 can be put in the sample setter 355a by the hand portion 351. Moe specifically, the sample feeding position is at an upper part of the rack conveying section 43 and closer to the direction of X2 than the sample container transfer portion 355. After the sample contained in the sample container 100 retained by the rack 101 at the sample feeding position is measured by the measurement unit 3, the rack conveying section 43 conveys the rack 101 at the sample feeding position to the post-analysis rack retaining section 42.

Figure 2:
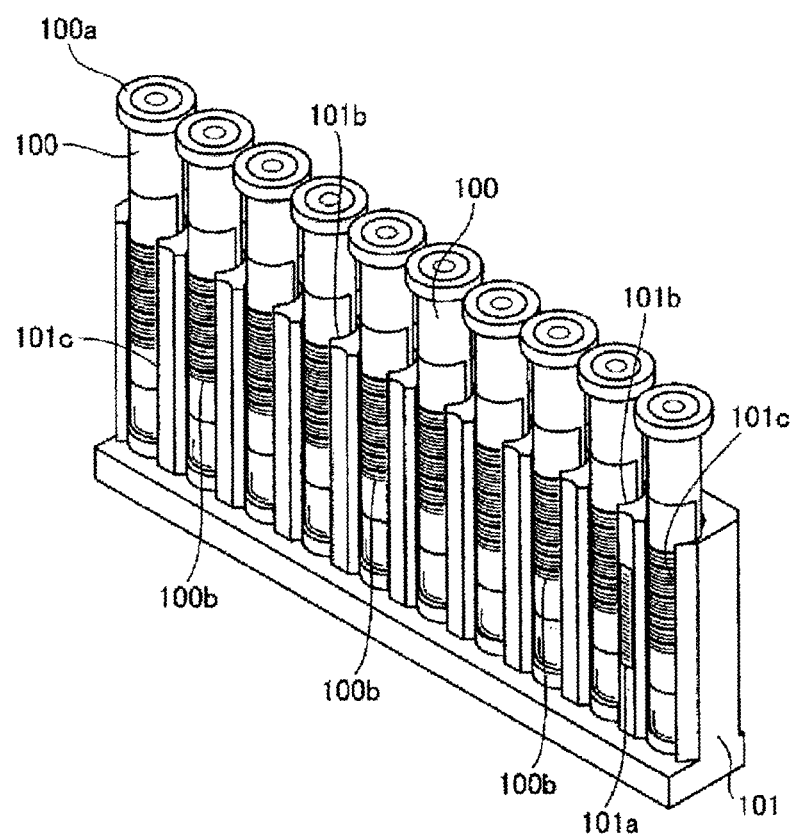
FIG. 2 is a perspective view illustrating external appearances of a rack retaining sample containers, and the sample containers retained in the rack.

FIG. 2 is a perspective view illustrating external appearances of the rack retaining therein the sample containers, and the sample containers retained in the rack. As illustrated in FIG. 2, 10 container housing parts 101b are formed in the rack 101 so that 10 sample containers 100 can be housed in an aligned manner. The barcode 100b of each sample container 100 is unique to each sample housed therein and is used, for example, for management of a test result of the sample. The container housing part 101b includes an opening 101c so that the barcode 100b of the housed sample container 100 can be visually confirmed. The barcode 101a of the rack 101 is unique to each rack and is used, for example, for management of test results of the samples housed therein.

Figure 3:
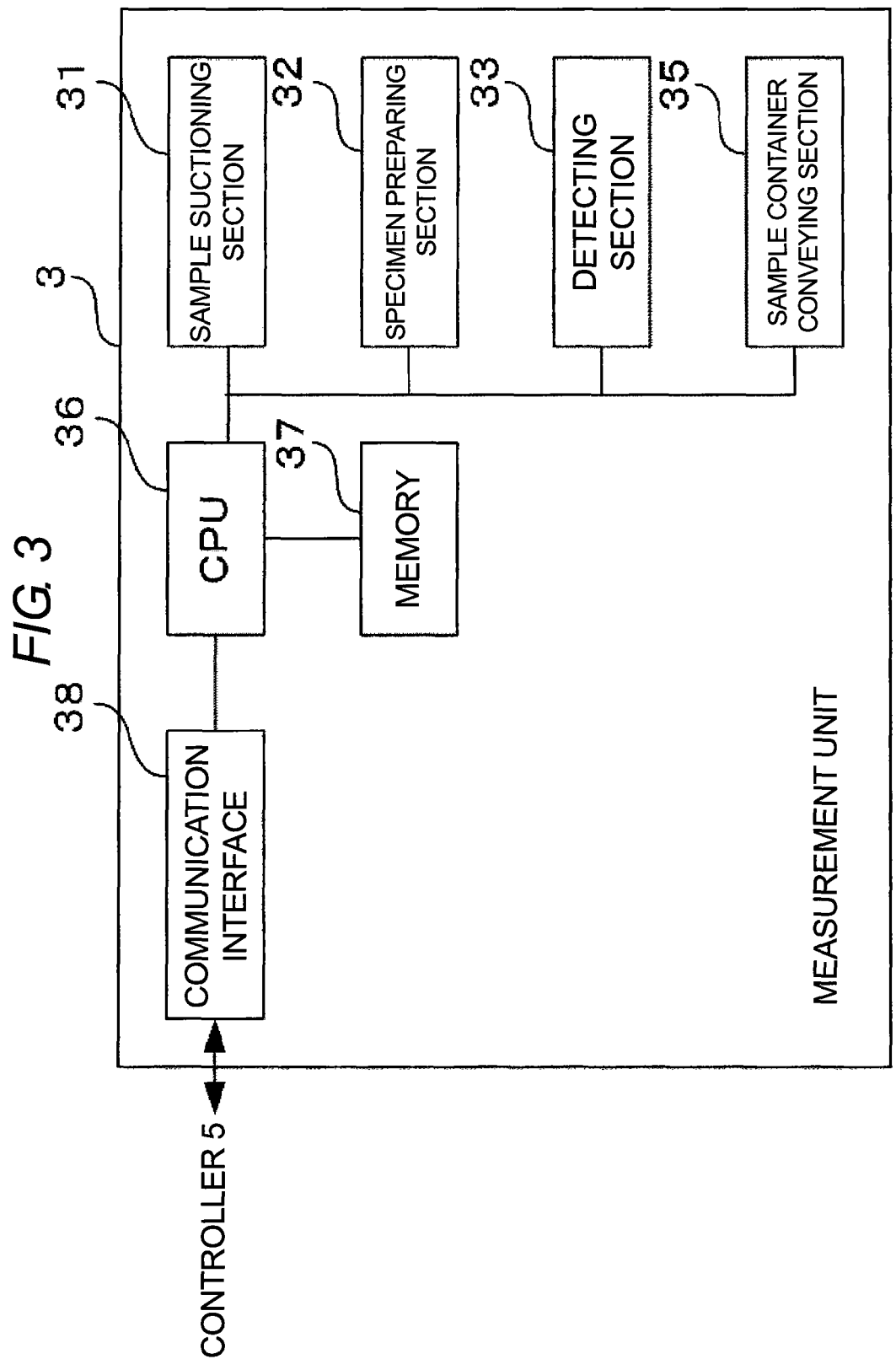
FIG. 3 is a block diagram illustrating a structure of a measurement unit according to the exemplary embodiment.

FIG. 3 is a block diagram illustrating a structure of the measurement unit 3 of the hemocyte analyzing apparatus 1. As illustrated in FIG. 3, the measurement unit 3 includes a sample suctioning section 31 for suctioning the sample (blood in the exemplary embodiment) from the sample container 100 placed at the sample suctioning position, a specimen preparing section 32 for preparing a specimen from the blood suctioned by the sample suctioning section 31, and a detecting section 33 for detecting, for example, particles of red blood cells included in the blood from the specimen prepared by the specimen preparing section 32. The detecting section 33 includes a flow cell 33a, which will be described later. The measurement unit 3 further includes a unit cover 34 provided to house therein the sample suctioning section 31 and the specimen preparing section 32, and a sample container conveying section 35 which fetches the sample container 100 into the unit cover 34 (see FIG. 1) to convey the sample container 100 to the sample suctioning position. The measurement unit 3 further includes a CPU 36 for controlling the respective sections, a memory 37 for storing therein programs run by the CPU 36 and data used to run the programs, and a communication interface 38 connected to the controller 5 to allow mutual communication therebetween.

Figure 4:
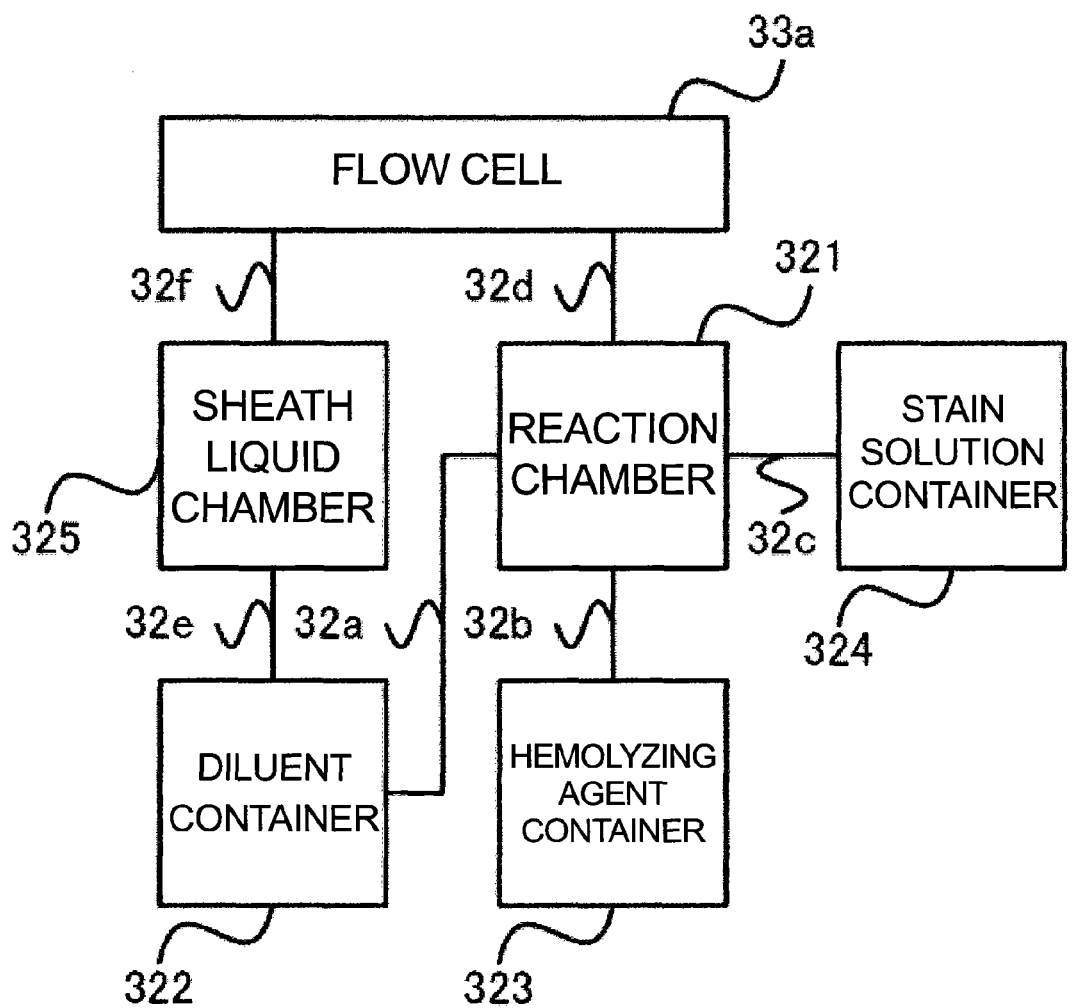
FIG. 4 is a block diagram schematically illustrating a structure of a specimen preparing section according to the exemplary embodiment.

FIG. 4 is a block diagram schematically illustrating a structure of the specimen preparing section 32. As illustrated in FIG. 4, the specimen preparing section 32 includes a reaction chamber 321 used to prepare the specimen, a diluent container 322 containing therein a diluent, a hemolyzing agent container 323 containing therein a hemolyzing agent, a stain solution container 324 containing therein a stain solution, and a sheath liquid chamber 325 storing therein a sheath liquid. The sample suctioning section 31 discharges the sample suctioned from the sample container 100 into the reaction chamber 321. The diluent container 322, hemolyzing agent container 323, and stain solution container 324 are respectively connected to the reaction chamber 321 through flow channels 32a, 32b and 32c provided in the form of a tube. The flow channels 32a, 32b and 32c are provided with a plurality of electromagnetic valves, and a diaphragm pump is provided among these electromagnetic valves. A positive pressure source and a negative pressure source are connected to the diaphragm pump so that the diaphragm pump is driven by a positive pressure or a negative pressure. When the electromagnetic valves and the diaphragm pump are activated, various reagents are selectively supplied to the reaction chamber 321. The reaction chamber 321 is connected to the flow cell 33a through a flow channel 32d.

The sheath liquid chamber 325 is provided to store therein the sheath liquid to be fed to the flow cell 33a and is connected to the diluent container 322 through a flow channel 32e including an electromagnetic valve. Prior to a measuring operation, the electromagnetic valves are opened, and the diluent contained in the diluent container 322 is supplied to the sheath liquid chamber 325. When the measurement starts, an electromagnetic valve provided in a flow channel 32f is opened in synchronization with the supply of the specimen to the flow cell 33a, and the sheath liquid of the sheath liquid chamber 325 is fed to the flow cell 33a through the flow channel 32f.

Returning to FIG. 3, the detecting section 33 includes the flow cell 33a (see FIG. 5), and thereby detects RBC (red blood cells) and PLT (platelets) according to sheath flow DC detection, and detect HGB (hemoglobin in blood) according to SLS-hemoglobin method. Further, the detecting section 33 detects WBC (white blood cells) according to flow cytometry using a semiconductor laser. A sample measurement result obtained by the detecting section 33 is transmitted by the CPU 36 to the controller 5. The measurement result is basic data of a final test result given to the user (number of red blood cells, number of platelets, hemoglobin concentration, and number of white blood cells).

Figure 5:
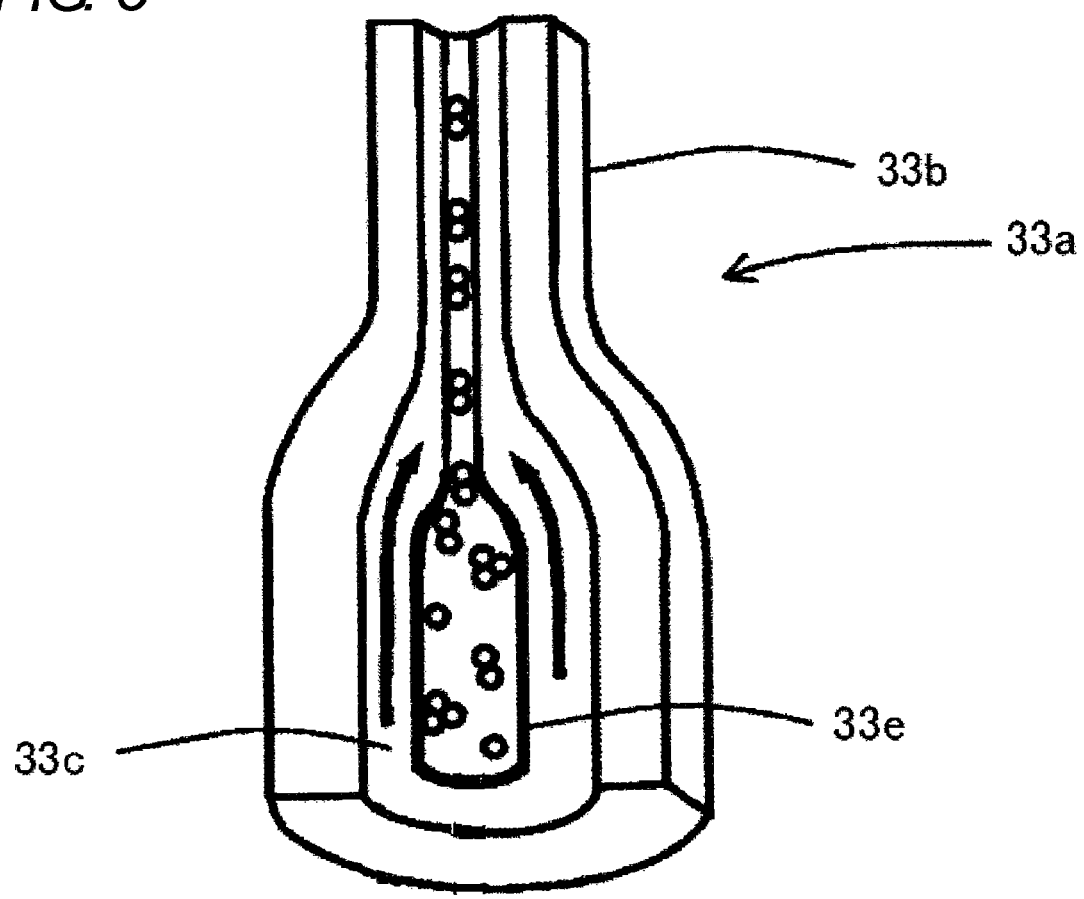
FIG. 5 is a perspective view illustrating a structure of a flow cell provided in a detecting section according to the exemplary embodiment.

FIG. 5 is a perspective view illustrating a structure of the flow cell 33a provided in the detecting section 33. As illustrated in FIG. 5, the flow cell 33a is formed in a tubular shape from a material, for example, translucent quarts, glass or synthetic resin. The inside of the flow cell 33a constitutes a flow channel through which the specimen and the sheath liquid are circulated. The flow cell 33a is provided with an orifice 33c whose internal space is narrower than any other parts thereof. An inlet area of the orifice 33c of the flow cell 33a includes a double tubular structure, and an inner tubular portion thereof serves as a specimen nozzle. The specimen nozzle is connected to the reaction chamber 321 through the flow channel 32d. The specimen is discharged through the specimen nozzle toward the orifice 33c.

An outer space of the specimen nozzle is a flow channel 33e for the sheath liquid to pass through. The flow channel 33e is connected to the sheath liquid chamber 325 through the flow channel 32f. The sheath liquid flows out of the sheath liquid chamber 325 and passes through the flow channel 33c by way of the flow channel 32f to be led into the orifice 33c. The sheath liquid thus supplied to the flow cell 33a flows so as to surround the specimen discharged from the specimen nozzle. The orifice 33c narrows down the specimen flow, and particles of red blood cells included in the specimen, for example, are encompassed by the sheath liquid, and one each of the particles passes through the orifice 33c.

Figure 6:
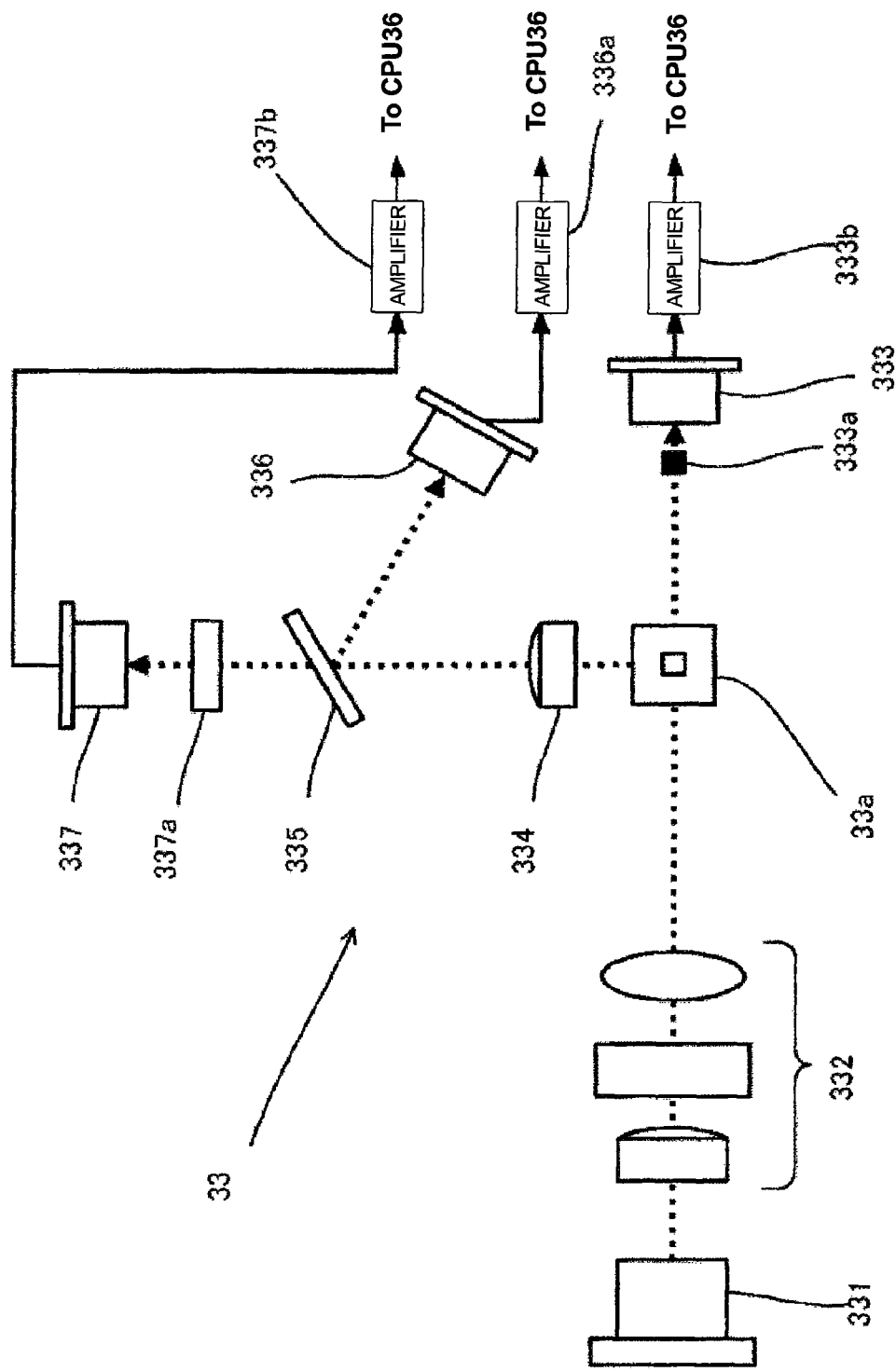
FIG. 6 is a drawing schematically illustrating a structure of the detecting section according to the exemplary embodiment.

FIG. 6 is a plan view schematically illustrating a structure of the detecting section 33. As illustrated in FIG. 6, the detecting section 33 is provided with a semiconductor laser light source 331 at such a position that a laser light is emitted therefrom toward the orifice 33b of the flow cell 33a. An irradiation lens system 332 having a plurality of lenses is disposed between the semiconductor laser light source 331 and the flow cell 33a. The irradiation lens system 332 converges collimated beams emitted from the semiconductor laser light source onto a beam spot. On an optical axis linearly extending from the semiconductor laser light source 331, a beam stopper 333a is provided so as to face the irradiation lens system 332 with the flow cell 33a interposed therebetween. Of the beams emitted from the semiconductor laser light source 331, a beam which is not scattered in the flow cell 33a but advances straight (hereinafter, referred to as direct beam) is blocked by the beam stopper 333a. A photodiode 333 is provided further down on a downstream side of the optical axis of the beam stopper 333a.

When the specimen is circulated in the flow cell 33a, the laser beam generates a scattered light signal and a fluorescent signal, and the photodiode 33 is irradiated with a signal beam advancing forward (scattered light). Of the beams advancing along the optical axis linearly extending from the semiconductor laser light source 331, the direct beam of the semiconductor laser light source 331 is blocked by the beam stopper 333a, and the scattered light advancing along the optical axis (hereinafter, referred to as forward scattered light) alone mostly enters the photodiode 333. The forward scattered light emitted from the flow cell 33a is photoelectrically converted by the photodiode 333, and an electrical signal thereby generated (hereinafter, referred to as "forward scattered light signal") is amplified by an amplifier 333b and then outputted to the CPU 36. The forward scattered light signal reflects the dimension of a hemocyte.

A side condensing lens 334 is provided on one side of the flow cell 33a in a direction orthogonal to the optical axis linearly extending from the semiconductor laser light source 331 toward the photodiode 333. A side light generated when the hemocyte passing through the flow cell 33a is irradiated with the semiconductor laser (light emitted in the direction orthogonal to the optical axis) is focused by the side condensing lens 334. A dichroic mirror 335 is provided on a downstream side of the side condensing lens 334. The dichroic mirror 335 divides the signal beam sent from the side condensing lens 334 into a scattered light component and a fluorescent component. On a side of the dichroic mirror 335 (direction intersecting with an optical-axis direction which connects the side condensing lens 334 to the dichroic mirror 335, a photodiode 336 for receiving a side scattered light is provided. On an optical-axis downstream side of the dichroic mirror 335, an optical filter 337a and a photodiode 337 are provided.

The side scattered light component reflected by the dichroic mirror 335 is photo-electrically converted by the photodiode 336. An electrical signal generated by the photoelectric conversion (hereinafter, referred to as side scattered light signal) is amplified by the amplifier 336a and then outputted to the CPU 36. The side scattered light signal reflects internal information of the hemocyte (for example, dimension of nucleus). The side fluorescent light component that transmitted through the dichroic mirror 335 is photoelectrically converted by the photodiode 337 after its wavelength is selected by the optical filter 337a. An electrical signal generated by the photoelectric conversion (hereinafter, referred to as side fluorescent signal) is amplified by the amplifier 337a and then outputted to the CPU 36. The side fluorescent optical signal reflects information relating to a degree of stain of the hemocyte.

Figure 7:
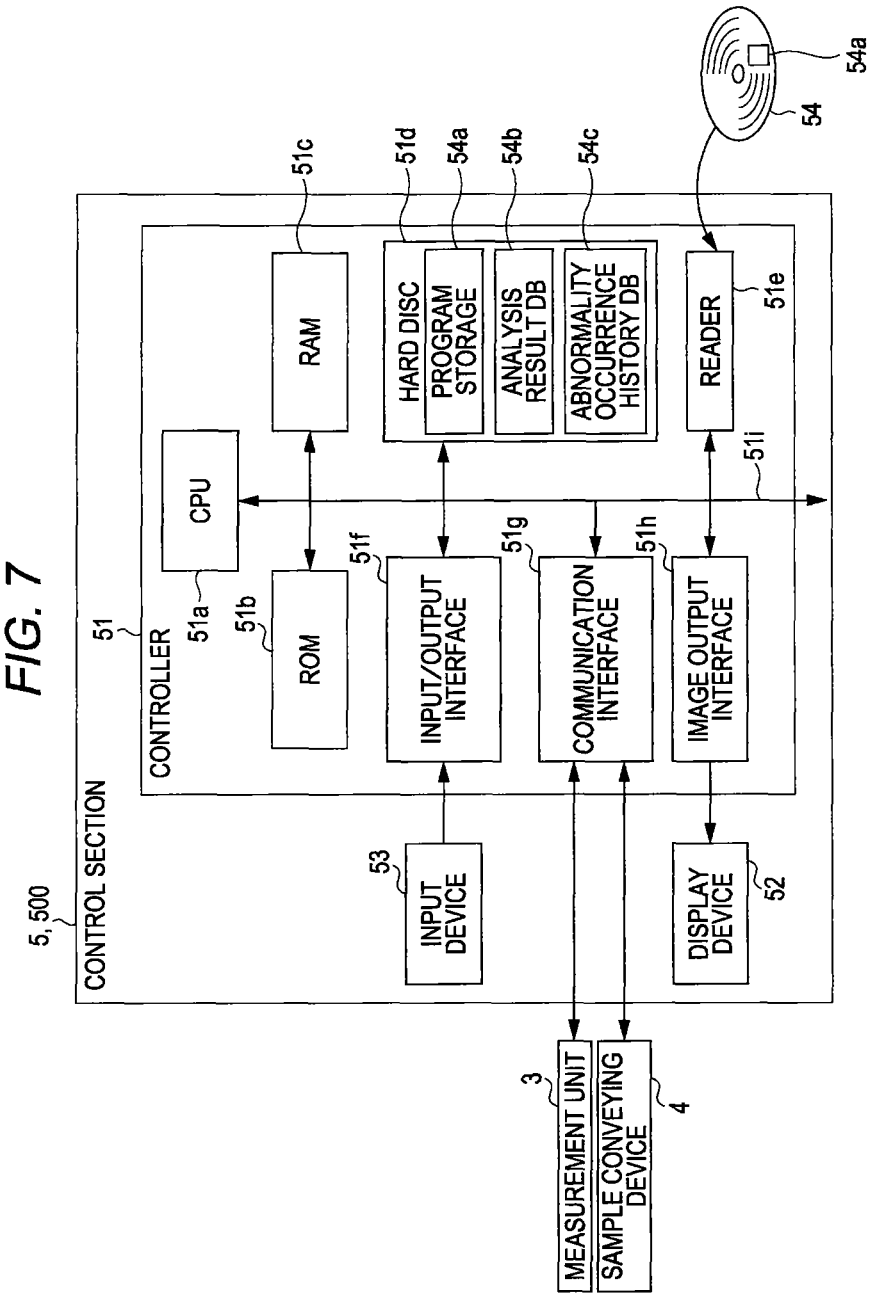
FIG. 7 is a block diagram illustrating a structure of a controller according to the exemplary embodiment.

FIG. 7 is a block diagram illustrating a structure of the controller 5 of the hemocyte analyzing apparatus 1. As illustrated in FIG. 7, a computer 500 having principal structural elements, such as a control device 51, a display device 52, and an input device 53, constitute the controller 5.

As illustrated in FIG. 7, principal structural elements constituting the control device 51 are a CPU 51a, a ROM 51b, a RAM 51c, a hard disc 51d, a readout device 51e, an input/output interface 51f, a communication interface 51g, and an image output interface 51h. The CPU 51a, ROM 51b, RAM 51c, hard disc 51d, readout device 51e, input/output interface 51f, communication interface 51g, and image output interface 51h are connected by a bus 51i.

The CPU 51a can run a computer program stored in the ROM 51b and a computer program stored into the RAM 51c. The computer 500 functions as the controller 5 when the CPU 51a runs an application program 54a which will be described later.

The ROM 51b includes, for example, mask ROM, PROM, EPROM, or EEPROM. The ROM 51b stores therein the computer program run by the CPU 51a and data used upon running the computer program.

The RAM 51c includes, for example, SRAM or DRAM. The RAM 51c is used to read the computer programs recorded in the ROM 51b and the hard disc 51d, and also used as a working region of the CPU 51a to run these computer programs.

The hard disc 51d includes a program storage 53a which stores therein various computer programs to be run by the CPU 51a such as an operating system and an application program, and data used to run the computer programs. The program storage 53a further stores therein an analysis program for the controller 5. The hard disc 51d is provided with a analysis result database 54b and an abnormality occurrence history database 54c.

The readout device 51e includes, for example, a flexible disc drive, CD-ROM drive or DVD-ROM drive. The readout device 51e can read a computer program or data recorded on a transportable recording medium 54. The transportable recording medium 54 further stores therein an application program. The computer 500 can read the application program from the transportable recording medium 54 and store the read application program in the program storage 53a.

The application program may be thus supplied from the transportable recording medium 54, or may be supplied from an external apparatus communicatably connected to the computer 500 by an electric communication line (either cable or wireless) through the electric communication line. For instance, the application program may be stored in a hard disc of a server computer on the Internet, which allows the computer 500 to access the server computer to download the application program and store the read application program in the program storage 53a.

In the program storage 53a, an operating system which provides a graphical user interface environment, for example, Windows (registered trademark) manufactured and sold by US Microsoft Corporation, is further installed. In the description given below, the application program is run on the operating system.

The input/output interface 51f includes, for example, serial interfaces such as USB, IEEE1394 and RS-232C, parallel interfaces such as SCSI, IDE and IEEE1284, and analog interfaces such as D/A converter and A/D converter. The input device 53 is connected to the input/output interface 51f. The user can input data to the computer 500 by manipulating the input device 53.

An example of the communication interface 51g is the Ethernet (registered trademark) interface. The computer 500 can transmit and receive data to and from the measurement unit 3 and the conveying unit 4 using a predefined communication protocol through the communication interface 51g.

The image output interface 51h is connected to the display 52 including LCD or CRT to output a video signal that accords with image data supplied from the CPU 51a to the display device 52. The display device 52 displays an image (screen) based on the inputted video signal.

Figure 8:
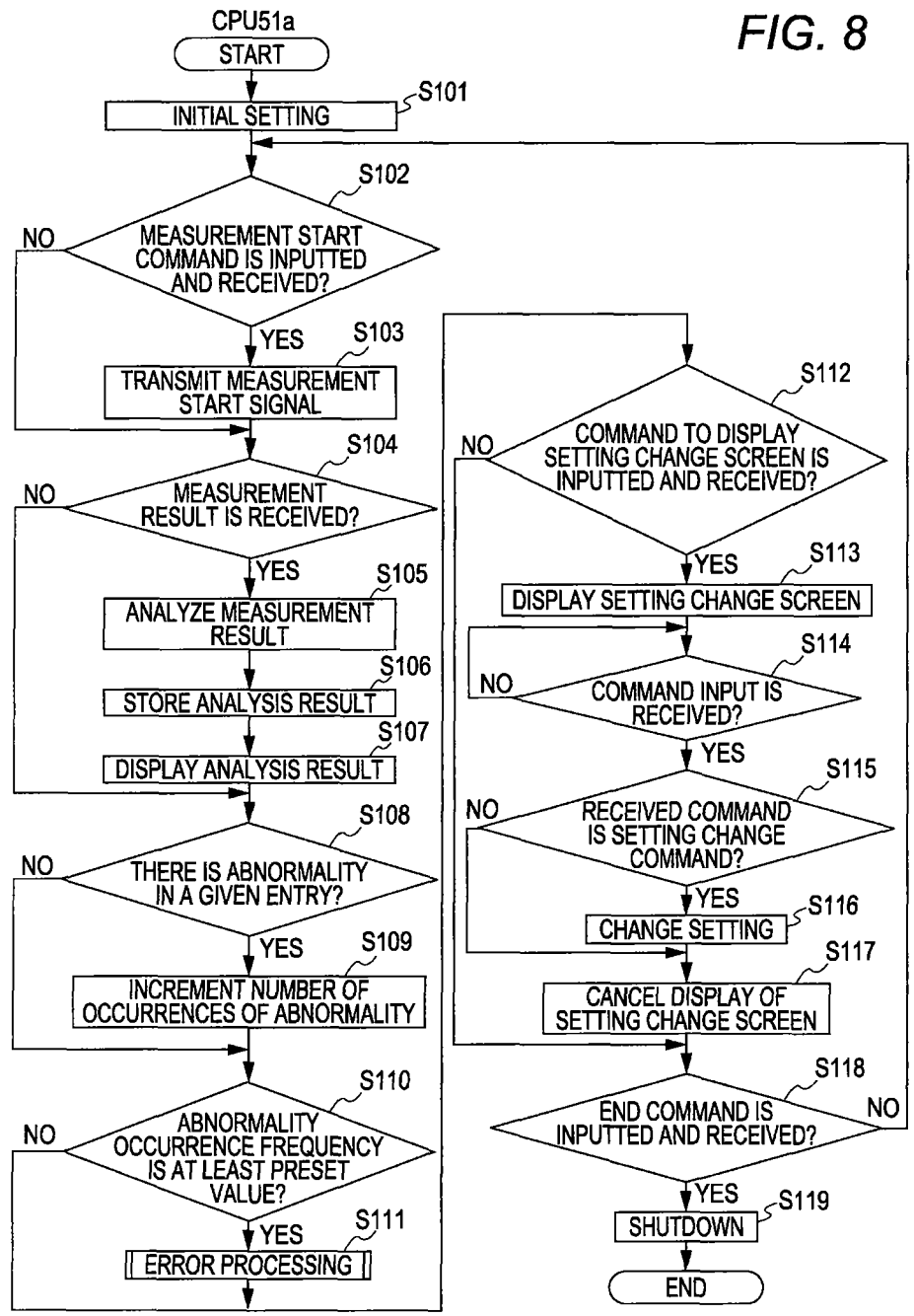
FIG. 8 is a flow chart illustrating sample analyzing steps carried out by the controller according to the exemplary embodiment.

FIG. 8 is a flow chart illustrating sample analyzing steps carried out by the controller 5. Hereinafter, the sample analyzing steps carried out by the CPU 51a are described referring to FIG. 8.

When the hemocyte analyzing apparatus 1 is turned on, the CPU 51a runs the analysis program stored in the program storage 53a. First, the CPU 51a carries out a processing step for initial setting such as setting various parameters (Step S101). Then, the CPU 51a determines whether or not a measurement start command input is received (Step S102). The user can input the measurement start command via the input device 53. When it is determined that the measurement start command is inputted and received (YES in Step S102), the CPU 51a transmits a measurement start signal to the measurement unit 3 and the conveying unit 4 (Step S103).

When it is determined that the measurement start command was not inputted and received (NO in Step S102) or transmitted the measurement start signal to the measurement unit 3, the CPU 51a determines whether or not a measurement result transmitted from the measurement unit 3 is received (Step S104). When it is determined that the measurement result was not received (NO in Step S104), the CPU 51a carries out a processing step of Step S108 described later. When it is determined that the measurement result is received (YES in Step S104), the CPU 51a analyzes the received measurement result (Step S105) and stores an analysis result thus obtained in the analysis result database 54b (Step S106). Then, the CPU 51a makes the display device 53 display thereon an analysis result display screen 521 showing analysis results stored in the analysis result database 54b (see FIG. 9) (Step S107).

Figure 9:
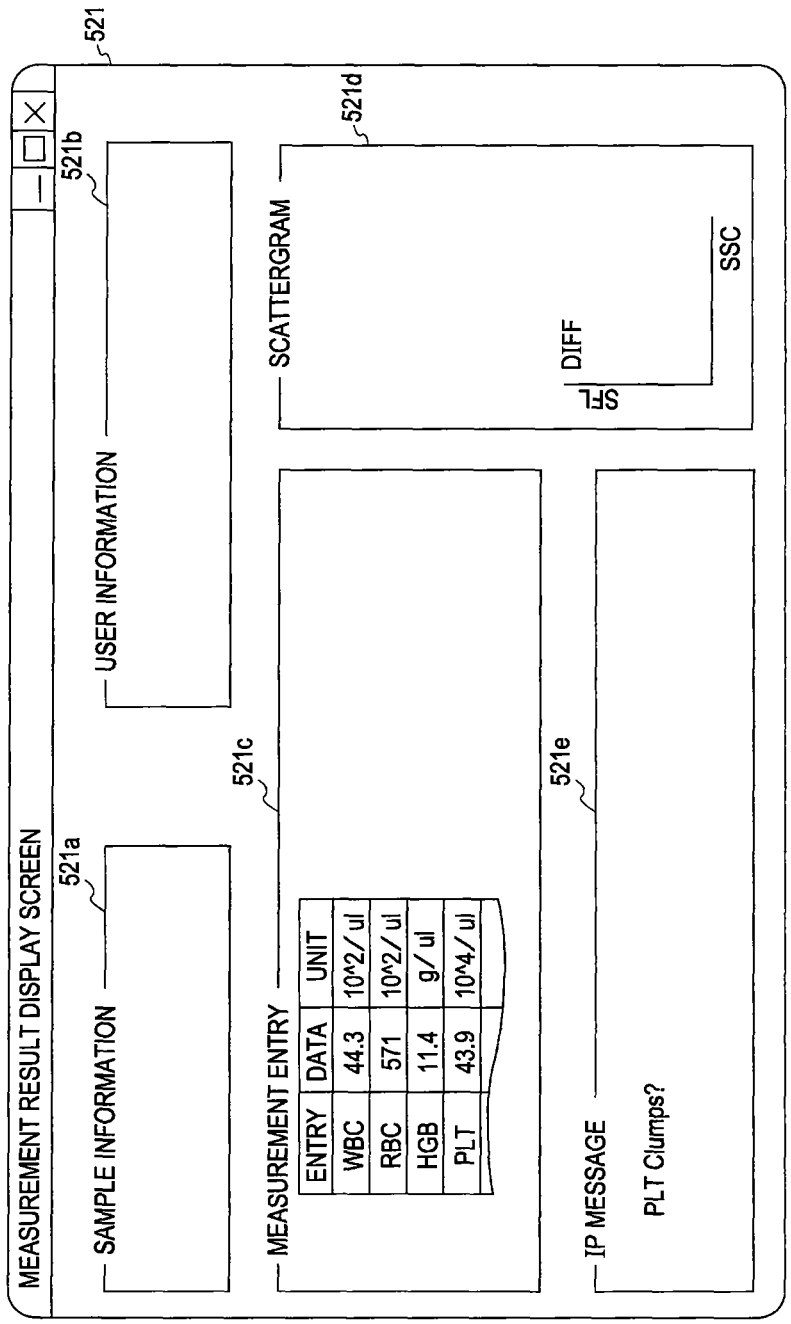
FIG. 9 illustrates an analysis result display screen displayed on a display device according to the exemplary embodiment.

FIG. 9 illustrates an example of the analysis result display screen 521. As illustrated in FIG. 9, the analysis result display screen 521 includes a sample information field 521a, a user information field 521b, a measurement component field 521c, a scattergram field 521d, and an IP message field 521e on which an IP message is displayed.

The sample information field 521a displays information of a sample such as ID of the measured sample. The user information field 521b displays information of a user such as ID of the user who operated the hemocyte analyzing apparatus 1 when the sample was measured.

The measurement component field 521c displays information of components included in the sample such as number of white blood cells (WBC), number of red blood cells (RBC), hemoglobin concentration (HGB), and number of platelets (PLT). The scattergram 521d displays, for instance, a DIFF scattergram in which a longitudinal axis represents a side fluorescence intensity, and a lateral axis represents a side scattered light intensity.

The IP message field 521e displays an IP message, for instance, IP message indicating an abnormal status in the case where the sample analysis result shows the abnormal status or the abnormal status is suspected. If a numeral value of a given measurement component in the analysis result is outside of its normal range or it is suspected that the value is outside of the normal range, the IP message is displayed on the IP message field 521e. There are two types of the IP messages; abnormal IP message indicating that the analysis result definitely includes abnormality, and suspect IP message indicating that the abnormality is suspected. For any analysis results including neither abnormality nor suspicion of the abnormality, none of the IP messages is displayed on the IP message field 521e.

Returning to FIG. 8, the CPU 51 determines whether or not a given measurement component in the analysis result stored in the analysis result database 54b shows an abnormal status (Step S108). In the present exemplary embodiment, the CPU 51a determines whether or not any abnormality is detected in the entry of platelets in the analysis result. In the case where the given component in the analysis result is confirmed as undergoing abnormality, a message indicating the abnormality is displayed on the IP message field 521e of the analysis result display screen 521. For instance, if it is suspected that platelet aggregation occurs in the collected sample, a suspect IP message "PLT Clumps?" indicating the suspicion of platelet aggregation is displayed on the IP message field 521e.

When it is determined that there is no abnormality in the analysis result, in other words, there is no message displayed on the IP message field 521e (NO in Step S108), the CPU 51a carries out a processing of Step S110 described later. When it is determined that there is an abnormality in the analysis result, in other words, the message is displayed on the IP message field 521e (YES in Step S108), the CPU 51a increments number of occurrences of the entry in the abnormality occurrence history database 54c (see FIG. 10) corresponding to the abnormality detected in the analysis result (Step S109).

FIG. 10 illustrates the abnormality occurrence history database 54c provided in the hard disc 51d. As illustrated in FIG. 10, the abnormality occurrence history database 54c includes fields which respectively show entries and number of occurrences of the respective entries. The entry shows what kind of abnormality was detected in the analysis result. In the present exemplary embodiment, any messages displayed on the IP message field 521e are registered in the entry field. The number of occurrences shows number of times when the abnormality occurred. In the present exemplary embodiment, the number of occurrences shows number of times when the message registered in the entry field is displayed on the IP message field 521e. When "PLT Clumps?" is displayed in the IP message field 522e of the analysis result display screen 522, for example, the CPU 51a increments the number of occurrences of "PLT Clumps?" registered in the abnormality occurrence history database 54c.

Referring to FIG. 8, the CPU 51a refers to the abnormality occurrence history database 54c to determine whether or not any of the entries shows the number of occurrences equal to or greater than a preset value (Step S110). The CPU 51a constantly counts the number of the analysis results so far obtained, and determines whether or not any of the entries shows the number of occurrences equal to or greater than the preset value based on the counting result and the number of occurrences of each entry in the abnormality occurrence history database 54c. The preset value is defined for each entry and previously stored in the hard disc 51d. For instance, the preset value may be checked for one sample per 20 samples, one sample per 10 samples, or one sample per five samples. The preset value may be a fixed value or a variable value. According to the present exemplary embodiment, the preset value can be changed, which will be described later.

When determining that none of the entries shows the number of occurrences equal to or greater than the preset value (NO in Step S110), the CPU 51a carries out a processing of Step S112 described later. When it is determined that any of the entries shows the number of occurrences equal to or greater than the preset value (YES in Step S110), the CPU 51a carries out an error processing (Step S111).

Figure 11:
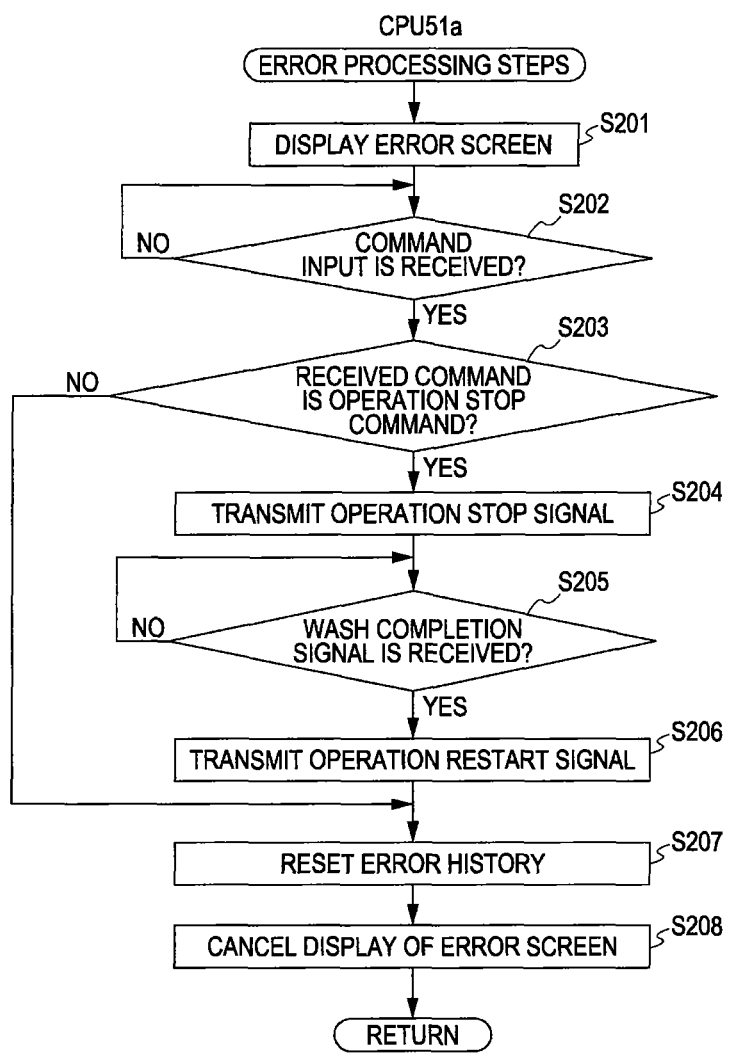
FIG. 11 is a flow chart illustrating error processing steps carried out by the controller according to the exemplary embodiment.

FIG. 11 is a flow chart illustrating error processing steps. Below is described the error processing steps referring to FIG. 11.

First, the CPU 51a makes the display device 52 display thereon an error screen 522 (see FIG. 12) (Step S201).

Figure 12:
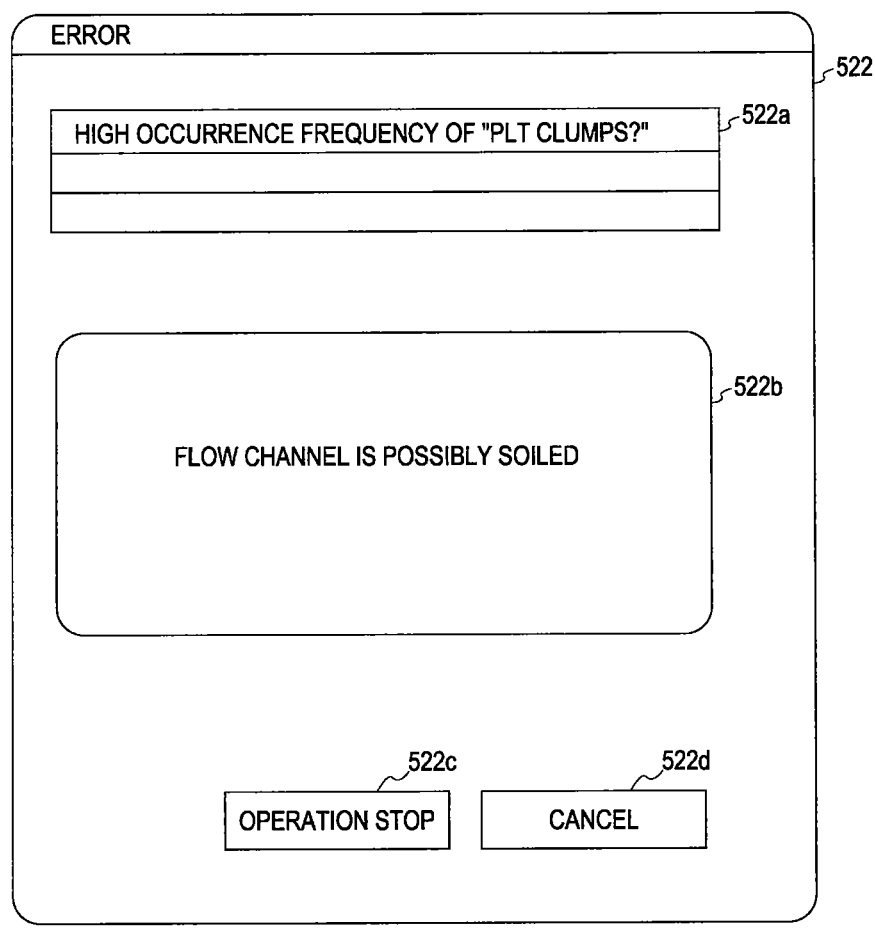
FIG. 12 illustrates an error screen displayed on the display device according to the exemplary embodiment.

FIG. 12 illustrates an example of the error screen 522 displayed on the display device 52. As illustrated in FIG. 12, the error screen 522 includes an error message region 522a and an abnormality-related message region 522b. The error message 522a displays an error message indicating which of the entries registered in the abnormality occurrence history database 54c shows the number of occurrences equal to or greater than the preset value. In the present exemplary embodiment, the error message displayed in the error message region 522a is linked to the message displayed in the IP message field 521e and then stored in the hard disc 51d.

The abnormality-related message region 522b displays a message indicating a sign of abnormality relating to the message displayed in the error message region 522a. For instance, in the event that the error message region 522a displays "high number of occurrences in "PLT Clumps?", a message, "a flow channel is possibly soiled" is displayed in the abnormality-related message region 522b. The message displayed in the abnormality-related message region 3 stored in the hard disc 51d.

The error screen 522 further includes an operation stop button 522c for transmitting a signal to stop the operations of the measurement unit 3 and the conveying unit 4, and a cancel button 522d. The user can input an operation stop command by selecting the operation stop button 522c using the input device 53. The user can input an error cancel command by selecting the cancel button 522d.

Returning to FIG. 11, the CPU 51a determines whether or not the operation stop command or the error cancel command is inputted and received (Step S202). When it is determined that one of the commands was inputted and received (YES in Step S202), the CPU 51a determines whether or not the received command is the operation stop command for stopping the operations of the measurement unit 3 and the conveying unit 4 (Step S203). When it is determined that the received command is not the operation stop command (NO in Step S203), the CPU 51a carries out a processing of Step S207 described later.

When it is determined that the received command is the operation stop command (YES in Step S203), the CPU 51a transmits the operation stop command to the measurement unit 3 and the conveying unit 4 (Step S204). When the measurement unit 3 and the conveying unit 4 receive the operation stop command, they respectively stop their operations; sample measuring operation, and sample conveying operation. The measurement unit 3 further executes a wash of the flow channel, which will be described later.

The CPU 51a determines whether or not a wash completion signal transmitted from the measurement unit 3 is received (Step S205). When it is determined that the wash completion signal is received (YES in Step S205), the CPU 51a transmits an operation start signal to the measurement unit 3 and the conveying unit 4 (Step S206). When the measurement unit 3 and the conveying unit 4 receive the operation start command, they respectively restart their sample measuring operation and sample conveying operation, which will be described later.

Then, the CPU 51a resets an error record (Step S207). The CPU 51a sets "0" in the number of occurrences of the entry in the abnormality occurrence history database 54c which is relevant to the message displayed in the error message region 522a of the error screen 522, and clears the number of the obtained analysis results. The CPU 51a thereafter cancels the display of the error screen 522 currently displayed on the display device 52 (Step S208), and then carries out the processing of Step S112.

Returning to FIG. 8, the CPU 51a determines whether or not a command to display a setting change screen is inputted and received (S112). The user can input the setting change screen display command via the input device 53. when it is determined that the setting change screen display command was not inputted and received (NO in Step S112), the CPU 51a carries out a processing of Step S118 described later. When it is determined that the setting change screen display command was inputted and received (YES in Step S112), the CPU 51a makes the display device 52 display thereon a setting change screen 523 (see FIG. 13) (Step S113).

Figure 13:
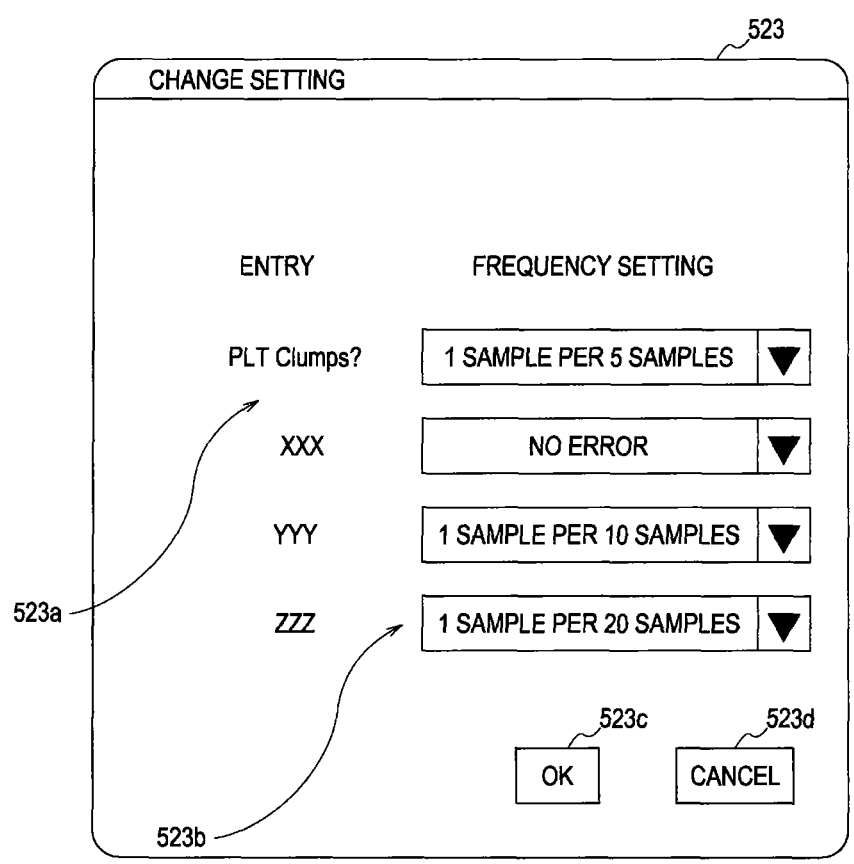
FIG. 13 illustrates a setting change screen displayed on the display device according to the exemplary embodiment.

FIG. 13 illustrates an example of the setting change screen 523 displayed on the display device 52. As illustrated in FIG. 13, the setting change screen 523 includes an entry field 523a which displays the entries registered in the abnormality occurrence history database 54c, and a frequency set field 523b to which preset values of frequency for the respective entries displayed on the entry field 523a are inputted.

The setting change screen 523 further includes an OK button 523c and a cancel button 523d. The user can settle an input to the frequency set field 523b by selecting the OK button 523c via the input device 53, more specifically, settle a setting change command input. The user can input a command to cancel the setting change by selecting the cancel button 523b.

The abnormality field 523a may be equipped with a function to register new entries in the abnormality occurrence history database 54c. More specifically, the user inputs a new entry to the entry field 523a via the input device 53, and then selects the OK button. The command to register the new entry is thus inputted, and the CPU 51a registers the new entry in the abnormality occurrence history database 54c based on the inputted command.

Referring to FIG. 8, the CPU 51a determines whether or not the setting change command or the setting cancel command is inputted and received (Step S114). When it is determined that one of the commands was inputted (YES in Step S114), the CPU 51a determines whether or not the received command is the setting change command (Step S115). When it is determined that the inputted command is the setting change command (YES in Step S115), the CPU 51a updates the setting based on the inputted setting change command (Step S116). The CPU 51a updates the preset values of the entries and stores the updated values in the hard disc 51d. When it is determined that the inputted command is not the setting change command, in other words, it is determined that the inputted command is the command to cancel the setting change (NO in Step S115), the CPU 51a cancels the display of the setting change screen 523 currently displayed on the display device 52 (Step S117).

Then, the CPU 51a determines whether or not an end command inputted by the user is received (Step S118). When it is determined that the end command is inputted and received (YES in Step S118), the CPU 51a transmits an end signal to the measurement unit 3 to carry out a shutdown process so that the operation of the controller 5 is ended (Step S119). When it is determined that end command is not inputted and received, (NO in Step S118), the CPU 51a carries out the processing of Step S102.

Figure 14:
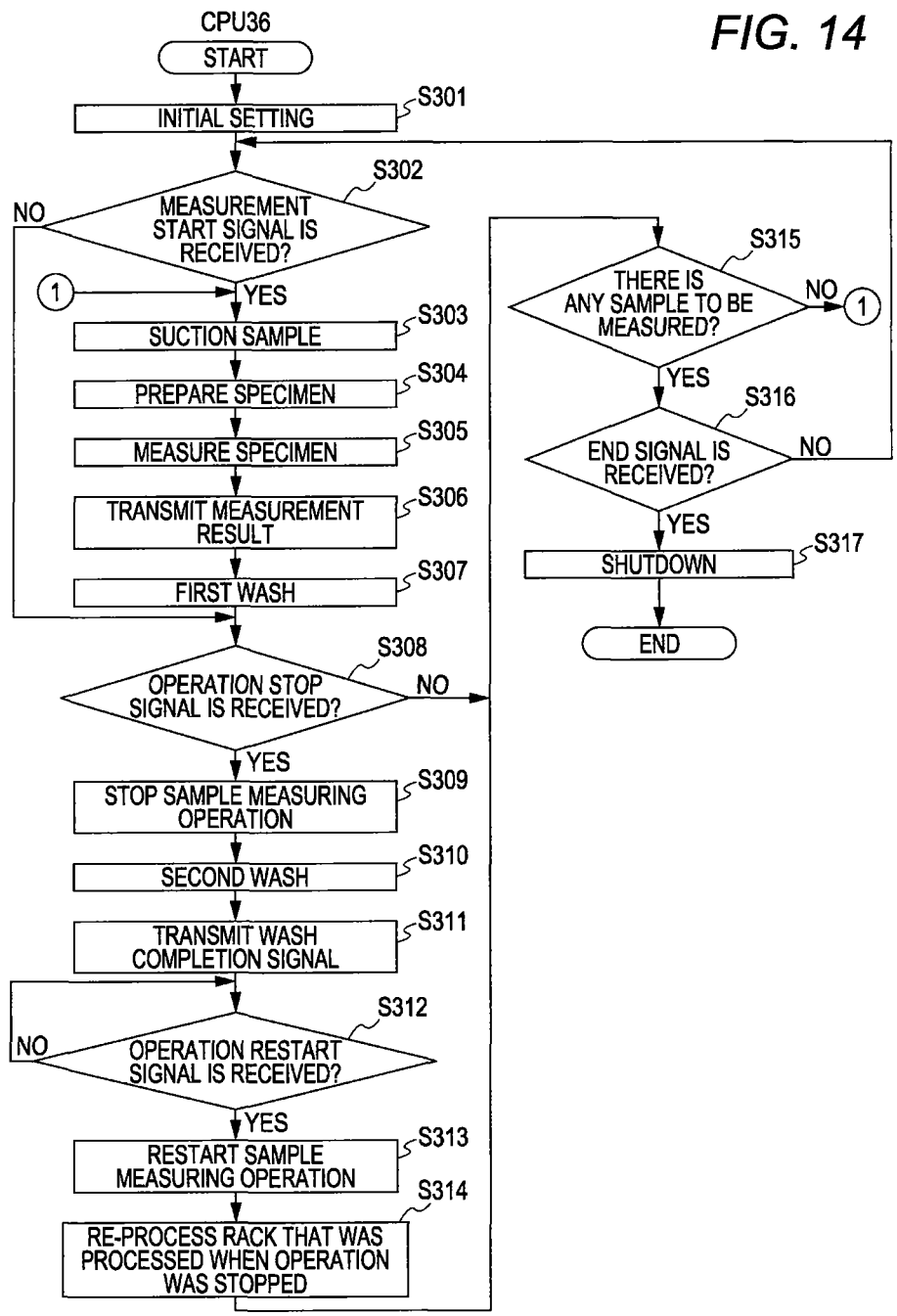
FIG. 14 is a flow chart illustrating sample measuring operations carried out by the measurement unit according to the exemplary embodiment.

FIG. 14 is a flow chart illustrating sample measuring operations carried out by the measurement unit 3. Hereinafter, the sample measuring operations carried out by the measurement unit 3 are described referring to FIG. 14.

To start with, the CPU 36 executes a processing step for initial setting such as returning the respective sections of the measurement unit 3 to their initial operating positions (Step S301). After the respective sections of the measurement unit 3 returned to their initial operating positions, the CPU 36 controls the specimen preparing section 32 to execute an early wash. More specifically, the CPU 36 controls the specimen preparing section 32 so that the diluent contained in the diluent container 322 and the hemolyzing agent contained in the hemolyzing agent container 323 flow into the reaction chamber 321, flow channel 32d, and flow cell 33a.

Then, the CPU 36 determines whether or not the measurement start signal transmitted from the controller 5 is received (Step S302). When it is determined that the measurement start signal was not received (NO in Step S302), the CPU 36 carries out a processing of Step S308 described later.

When it is determined that the measurement start signal is received (YES in Step S302), the CPU 36 controls the sample container conveying section 35 and the sample suctioning section 31 so that the sample housed in the sample container 100 retained in the rack 101 at the sample feeding position is suctioned (Step S303). Upon the reception of the measurement start signal transmitted from the controller 5, the conveying unit 4 transversely moves the rack 101 in the pre-analysis rack retaining section 41 in the direction of X1 using the rack conveying section 43 to deliver the rack 101 to the sample feeding position.

In Step S303, the CPU 36 controls the sample container conveying section 35 so that the sample container 100 retained in the rack 101 at the sample feeding position is set in the sample setter 355a by the hand portion 351, and the sample container 100 is finally delivered to the sample suctioning position by sliding the sample container transfer portion 355 in the direction of Y2. The CPU 36 controls the sample suctioning section 31 so that the sample is suctioned from the sample container 100 delivered to the sample suctioning position and discharged into the reaction chamber 321.

The CPU 36 then controls the specimen preparing section 32 so that the reagents are supplied to the reaction chamber 321 and mixed with the sample to prepare specimens (Step S304). The CPU 36 controls the detecting section 33 so that the specimens prepared by the specimen preparing section 32 are measured (Step S305). When the sample measurement is over, the CPU 36 transmits a measurement result thereby obtained to the controller 5 (Step S306).

The CPU 36 controls the specimen preparing section 32 to execute a first wash (Step S307). The CPU 36 controls the specimen preparing section 32 so that the diluent contained in the diluent container 322 flows into the reaction chamber 321, flow channel 32d, and flow cell 33a.

The processing steps S303 to S307 are parallelly carried out for each of the sample containers 100 retained in the rack 101 at the sample feeding position. Upon completion of the measurement of the samples housed in all of the sample containers 100 retained in the rack 101 at the sample feeding position, the conveying unit 4 transversely shifts the rack 101 at the sample feeding position in the direction of X1 using the rack conveying section 43 to deliver the rack 101 to the post-analysis retaining section 42.

The CPU 36 determines whether or not the operation stop signal transmitted from the controller 5 is received (Step S308). When it is determined that the operation stop signal was not received (NO in Step S308), the CPU 36 carries out a processing of Step S315 described later.

Figure 15:
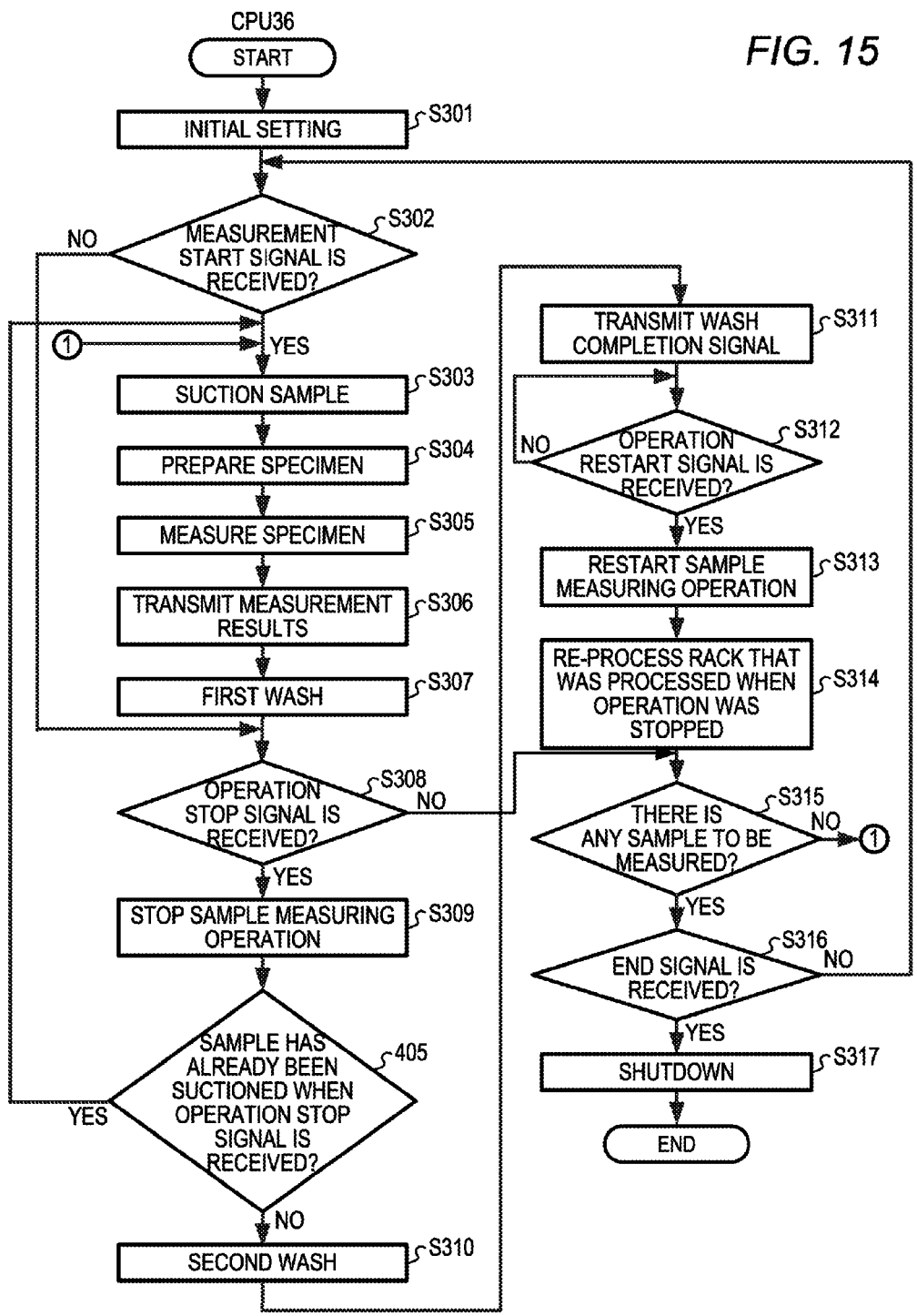
FIG. 15 is a flow chart illustrating sample measuring operations carried out by the measurement unit according to the exemplary embodiment.

When it is determined that the operation stop signal was received (YES in Step S308), the CPU 36 stops the sample measuring operation carried out by the measurement unit 3 (Step S309). The CPU 36 controls the sample container conveying section 35 so that the sample container transfer portion 355 slides in the direction of Y1 for causing the hand portion 351 to return the sample container 100 currently placed in the sample container setter 355a to the rack 101 at the sample feeding position. In the case where the sample has already been suctioned from the sample container 100 (S405) by the sample suctioning section 31 when the operation stop signal is received, the CPU 36 controls the respective sections to execute the measuring steps (Steps S303 to S307) executed to the suctioned sample, as shown in FIG. 15. When the operation stop signal transmitted from the controller 5 is received, and the sample container 100 is returned to the rack 101 at the sample feeding position, the conveying unit 4 transversely shifts the rack 101 in the direction of X2 (see FIG. 1) using the rack conveying section 43 to deliver the rack 101 to the pre-analysis rack retaining section 41.

The CPU 36 then controls the specimen preparing section 32 so that a second wash is executed (Step S310). The CPU 36 controls the specimen preparing section 32 so that the diluent contained in the diluent container 322 and the hemolyzing agent contained in the hemolyzing agent container 323 flow into the reaction chamber 321, flow channel 32d, and flow cell 33a. The hemolyzing agent includes a surface active agent. Therefore, the second wash exerts a more powerful washing performance than the first wash, thereby removing any residual soil in the flow channel that was left unwashed in the first wash. When the second wash is over, the CPU 36 transmits the wash completion signal to the controller 5 (Step S311).

The CPU 36 determines whether or not the operation start signal transmitted from the controller 5 is received (Step S312). When it is determined that the operation start signal was received (YES in Step S312), the CPU 36 restarts the sample measuring operation (Step S313). When the operation start signal transmitted from the controller 5 was received, the conveying unit 4 delivers the rack 101 in process by the measurement unit 3 when the measurement operation was discontinued from the pre-analysis rack retaining section 41 to the sample feeding position using the rack conveying section 43.

The CPU 36 executes the re-processing of the rack 101 in process when the measurement operation was discontinued (Step S314). The CPU 36 controls the respective sections so that the sample measuring operations (Steps S303-S307) are executed to the sample whose measurement result is not yet transmitted to the controller 5 among all of the samples housed in the sample containers 100 retained in the rack 101 at the sample feeding position. When the re-processing is over, the conveying unit 4 transversely shifts the rack 101 in the direction of X1 (see FIG. 1) using the rack conveying section 43 to convey the rack 101 to the post-analysis rack retaining section 42.

The CPU 36 then determines whether or not there are any other samples to be measured (Step S315). The CPU 36 determines whether there is any rack 101 to be conveyed from the pre-analysis rack retaining section 41 to the sample feeding position by the rack conveying section 43. When it is determined that there are samples to be measured (NO in Step S315), the CPU 36 carries out the processing of Step S303.

When it is determined that there is no sample to be measured (YES in Step S315), the CPU 36 determines whether or not the end signal transmitted from the controller 5 is received (Step S316). When it is determined that the end signal was not received (NO in Step S316), the CPU 36 carries out the processing of Step S302.

When it is determined that the end signal was received (YES in Step S316), the CPU 36 executes a shutdown wash and then ends the operation of the measurement unit 3 (Step S317). The CPU 36 controls the sample suctioning section 31 and the specimen preparing section 32 so that the flow channel is washed with a washing solution. Unlike the diluent or hemolyzing agent, the washing solution is a chemical agent specially prepared to wash the flow channel. Therefore, the shutdown wash exerts a more powerful washing performance than the first and second washes. The CPU 36 controls the sample suctioning section 31 so that the washing solution retained in a washing solution container is suctioned therefrom and discharged into the reaction chamber 321. After that, the CPU 36 controls the specimen preparing section 32 so that the washing solution discharged into the reaction chamber 321 flows into the flow channel 32d and the flow cell 33a.

As described so far, the automatic analyzing apparatus according to the present exemplary embodiment analyzes the sample measurement result from the measurement unit 3 to obtain the occurrence frequency of analysis results including information of some abnormality in a given sample component, and when the frequency exceeds a preset value, the automatic analyzing apparatus makes the display device 52 display thereon the screen including information indicating that the flow channel of the measurement unit 3 is possibly undergoing a problem. Thus, the automatic analyzing apparatus according to the present exemplary embodiment can provide information indicating a sign of any trouble that is possibly generated in the analyzing apparatus before the trouble actually happens.

The automatic analyzing apparatus according to the present exemplary embodiment can change the preset value of the occurrence frequency for each of the entries. Therefore, the automatic analyzing apparatus according to the present exemplary embodiment can provide information indicating a sign of any trouble that is possibly generated in the analyzing apparatus in accordance with conditions desired by the user.

When the occurrence frequency of analysis results including information of some abnormality in a given sample component exceeds the preset value while the samples are consecutively measured, the automatic analyzing apparatus according to the present exemplary embodiment stops the measurement operation by the measurement unit 3 and the conveying operation by the conveying unit 4 after the ongoing sample measurement at the time is completed. The automatic analyzing apparatus according to the present exemplary embodiment thus technically characterized can avoid producing an unreliable analysis result owing to any trouble generated therein.

Another Exemplary Embodiment

The embodiments disclosed herein are illustrative in all aspects. The scope of the invention is not defined by the description of the embodiments but should be solely defined by the appended Claims.

In the exemplary embodiment, the automatic analyzing apparatus is the hemocyte analyzing apparatus, however, the present invention is not necessarily limited thereto. Other examples of the automatic analyzing apparatus are; urine cell analyzing apparatus, immunity analyzing apparatus, blood coagulation measuring apparatus, hemogram analyzing apparatus, and biochemical analyzing apparatus. A particularly preferable example of the automatic analyzing apparatus is a urine cell analyzing apparatus and an immune analyzing apparatus provided with a fluid system in which a sample and reagents are circulated, wherein the sample is measured by flow cytometry.

In the exemplary embodiment, information of an abnormality detected in a given sample component is information of platelet aggregation. The information of platelet aggregation is information indicating that abnormal particles which are not included in an analysis result of a sample collected from a healthy test subject, in brief, aggregates of platelet, are included. However, the present invention is not necessarily limited thereto. For example, the information may be information indicating that any abnormal particles other than aggregates of platelet are included. The information of an abnormality detected in a given sample component may be information indicating that a count result of, for example, red blood cells or white blood cells is outside of its normal range. The information of an abnormality detected in a given sample component is, however, preferably information of any abnormality which is unlikely to occur in a conventional measuring operation.

In the exemplary embodiment, when the frequency of obtaining the analysis results including information of some abnormality in a given sample component exceeds the preset value, the screen including information indicating the same is displayed on the display device 52. However, the present invention is not necessarily limited thereto. For example, the controller 5 may be equipped with a speaker, and in this case, when the frequency of obtaining the analysis results including information of some abnormality in a given sample component exceeds the preset value, the CPU 51a controls the speaker so that a warning sound or a vocal message indicating the same is generated. This makes it unnecessary for the user to confirm the display device 52 to know there is a sign of any trouble that is generated in the apparatus.

In the exemplary embodiment, information of any abnormality in the flow channel is displayed in the abnormality-related message region 522b of the error screen 522. However, the present invention is not necessarily limited thereto. For example, the display device 52 may display information of a sign of an abnormality generated in any mechanisms other than the flow channel provided in the measurement unit 3 in the abnormality-related message region 522b of the error screen 522. Accordingly, the user can know a sign of any trouble in all of the mechanisms provided in the measurement unit 3.

In the exemplary embodiment, when the error message region 522a of the error screen 522 displays "high number of occurrences in "PLT Clumps?", the abnormality-related message region 522b displays such a message as "the flow channel is possibly soiled". However, the present invention is not necessarily limited thereto. When the error message region 522a displays "high number of occurrences in "PLT Clumps?", the abnormality-related message region 522b may display a message that encourages the user to execute a maintenance operation, for example, "please wash the flow channel". The abnormality-related message region 522b may display information of a maintenance operation of any mechanisms other than the flow channel provided in the measurement unit 3. This helps the user to readily know how to cope with the indicated sign of trouble.

In the second wash according to the exemplary embodiment, the diluent contained in the diluent container 322 and the hemolyzing agent contained in the hemolyzing agent container 323 are supplied into the reaction chamber 321, flow channel 32d, and flow cell 33a. However, the present invention is not necessarily limited thereto. The second wash may be a washing operation similar to the shutdown wash. More specifically, the second wash may be carried out such that the washing solution contained in the washing solution container is dispensed into the reaction chamber 321 by the sample suctioning section 31, and the washing solution dispensed into the reaction chamber 321 is circulated into the flow channel 32d and the flow cell 33a. This reduces the likelihood that the flow channel is soiled and any soil or dirt attached thereto is carried over.

In the exemplary embodiment, the error screen 522 is displayed on the display device 52 so that the user can choose to continue or stop the sample measuring operation by the measurement unit 3 and the sample conveying operation by the conveying section 4. However, the present invention is not necessarily limited thereto. For example, the CPU 51a may be configured to automatically transmit the stop signals of the sample measuring operation and the sample conveying operation to the measurement unit 3 and the conveying section 4, respectively, in place of displaying the error screen 522 on the display device 52. When the measurement unit 3 receives the stop signals transmitted from the controller 5, the second wash may be automatically carried out in the flow channel. When the measurement unit 3 receives the stop signals transmitted from the controller 5, the measurement unit 3 may automatically execute not only the wash of the flow channel but also the maintenance of any mechanisms other than the flow channel provided in the measurement unit 3. With this configuration, the wash is automatically executed as soon as a sign of any trouble is detected in the analyzing apparatus such as the soiled flow channel. As a result, possible troubles of the apparatus can be prevented from happening.

What is claimed is:

1. An analyzing apparatus comprising a processor of a controller and a memory that stores programs executable by the processor to:
   receive a test result on a test item from a measurement unit configured to test a blood sample collected from a test subject on at least one test item, the measurement unit comprising:
      a sample suctioning section configured to suction the blood sample from a sample container;
      a chamber configured to prepare a specimen from the blood sample suctioned by the sample suctioning section and a reagent;
      a flow cell configured to flow the specimen prepared by the chamber; and
      a flow path configured to connect the chamber and the flow cell, the flow path supplying the specimen prepared by the chamber to the flow cell;
   analyze the test result to determine whether the test result includes platelet aggregation;
   if the test result is determined to include the platelet aggregation, update a history database in which a history of determinations of platelet aggregation is recorded;
   review the updated history database to determine whether a frequency of the determinations of platelet aggregation exceeds a predetermined frequency; and
   if the frequency of the determinations of platelet aggregation is determined to exceed the predetermined frequency, output an alert on a possible problem sustained by the flow path of the measurement unit, wherein the alert is not output upon the frequency of the determination of platelet aggregation being less than the predetermined frequency.

2. The analyzing apparatus according to claim 1, wherein the processor alerts a user with a notice indicating the test item and comprising at least one of (i) a possible cause for the possible problem and (ii) an instruction to remove the possible problem from the measurement unit.

3. The analyzing apparatus according to claim 1, wherein the processor alerts a user with an option selectable by a user to stop an operation of the measurement unit.

4. The analyzing apparatus according to claim 1, wherein the processor changes the predetermined frequency according to an instruction from a user.

5. The analyzing apparatus according to claim 4, wherein the processor changes the predetermined frequency according to an instruction received from a user via a graphic user interface.

6. The analyzing apparatus according to claim 1, wherein the test result includes one of (i) the platelet aggregation is found on the test result and (ii) the platelet aggregation is suspected on the test result, and the processor updates the history database only when the test result is determined to include that the platelet aggregation is found on the test result.

7. The analyzing apparatus according to claim 1, wherein the test item is selected from a group of test items, test results on which exhibit abnormalities at a relatively low frequency.

8. A method for detecting a possible problem of an analyzing apparatus, comprising computer executable steps executed by a processor of a controller to implement:
receiving, using the processor, a test result on a test item from a measurement unit configured to test a sample collected from a test subject on at least one test item, the measurement unit comprising:
a sample suction section configured to suction the sample from a sample container;
a chamber configured to prepare a specimen from the sample suctioned by the sample suctioning section and a reagent;
a flow cell configured to flow the specimen prepared by the chamber; and
a flow path configured to connect the chamber and the flow cell, the flow path supplying the specimen prepared by the chamber to the flow cell;
analyzing, using the processor, the test result to determine whether the test result includes platelet aggregation;
if the test result is determined to include the platelet aggregation, updating, using the processor, a history database in which a history of determinations of platelet aggregation is recorded;
reviewing, using the processor, the updated history database to determine whether a frequency of the determinations of platelet aggregation exceeds a predetermined frequency; and
if the frequency of the determinations of platelet aggregation is determined to exceed the predetermined frequency, outputting an alert, using the processor, on a possible problem sustained by the flow path of the measurement unit,
wherein the alert is not output upon the frequency of the determinations of platelet aggregation being less than the predetermined frequency.

9. The analyzing apparatus according to claim 1, wherein the history database comprises a number of the determinations of platelet aggregation.

10. A non-transitory storage medium which comprises programs executable by a processor of a controller to:
receive a test result on a test item from a measurement unit configured to test a blood sample collected from a test subject on at least one test item, the measurement unit comprising:
a sample suction section configured to suction the blood sample from a sample container;
a chamber configured to prepare a specimen from the sample suctioned by the sample suctioning section and a reagent;
a flow cell configured to flow the specimen prepared by the chamber; and
a flow path configured to connect the chamber and the flow cell, the flow path supplying the specimen prepared by the chamber to the flow cell;
analyze the test result to determine whether the test result includes platelet aggregation;
if the test result is determined to include the platelet aggregation, update a history database in which a history of determinations of platelet aggregation is recorded;
review the updated history database to determine whether a frequency of the determinations of platelet aggregation exceeds a predetermined frequency; and measurement unit,
wherein the alert is not output upon the frequency of the determinations of platelet aggregation being less than the predetermined frequency;
if the frequency of the determinations of platelet aggregation is determined to exceed the predetermined frequency, output an alert on a possible problem sustained by the flow path of the measurement unit,
wherein the alert is not output upon the frequency of the determinations of platelet aggregation being less than the predetermined frequency.

* * * * *